US00PP13735P29

(12) United States Plant Patent
Lemon

(10) Patent No.: US PP13,735 P2
(45) Date of Patent: Apr. 22, 2003

(54) GERANIUM PLANT NAMED 'PATRIOT CRANBERRY RED'

(75) Inventor: David Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,065

(22) Filed: Sep. 17, 2002

(51) Int. Cl.[7] ..... A01H 5/00
(52) U.S. Cl. ..... Plt./330
(58) Field of Search ..... Plt./330

*Primary Examiner*—Kent Bell
(74) *Attorney, Agent, or Firm*—Webb Ziesenhiem Logsdon Orkin & Hanson, P.C.

(57) ABSTRACT

A new and distinct very early flowering geranium plant with distinctive cranberry red colored flowers above medium green foliage.

1 Drawing Sheet

BOTANICAL CLASSIFICATION

*Pelargonium×hortorum* (zonal geranium).

VARIETAL DENOMINATION

'Patriot Cranberry Red'.

BACKGROUND OF THE INVENTION

The present invention comprises a new and distinct cultivar of *Pelargonium×hortorum* known by the varietal name 'Patriot Cranberry Red'. The new variety was discovered in a selected breeding program in Lompoc, Calif. as Breeder No. 6DG2815-1. The new variety is a result of cross breeding of 'Americana Dark Red' (female) (U.S. Plant Pat. No. 9,307) and 'BFP-838 Dark Red' (male) (U.S. Plant Pat. No. 9,544). The new variety exhibits similar plant type to both parents and a flower color with more blue pigment than the parents' flower colors. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 8 weeks from a rooted cutting to flowering in a 6 inch pot. The response time was determined on plants grown in soilless media employing constant fertilizer 200–250 parts per million of nitrogen and potassium in full light.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants described were about 8 weeks from a rooted cutting. The color readings were taken on a plant under 65–85 foot candles of fluorescent cool white light. Color references are primarily to The R.H.S. Colour Chart of The Royal Horticultural Society of London.

PLANT

Form: Medium mound; free basal branching.
Height: 19–23 cm from media surface to top of foliage in a 16 cm pot.
Diameter: 20–24 cm.
Strength: Does not require artificial support.
Rooting time: Roots visible to outside of a dirt plug in 10–14 days.
Leaves:
- *Arrangement.*—Alternate.
- *Stipules.*—Two per node.
- *Size.*—Length: 6.5–7.5 cm. Width: 7.5–8.5 cm. Zone: 2 mm from petiole attachment; zone is 1 cm wide.
- *Shape.*—Reniform; cordate base.
- *Apex.*—Rounded.
- *Margin.*—Crenate.
- *Texture.*—Velvety; pubescent.
- *Color.*—Upper surface: 137A. Lower surface: 137C. Zone: Faint but visible as 147A upon close inspection.
- *Ribs and veins.*—Venation: Palmate. Color: 144A.

Petioles:
- *Color.*—144A.
- *Length.*—6.5–9 cm.

Stem:
- *Color.*—114B.
- *Internode length.*—1.5–3.5 cm.

THE BUD

Shape when no color showing:
- *Overall.*—Elliptical cluster.
- *Individual bud.*—Elliptical or oval.

Size when no color showing:
- *Overall.*—3.5–4.5 cm across cluster.
- *Individual bud.*—1.0–1.5 cm long and 5–6 mm in diameter.

Number of buds per cluster: 26–35.
Color: 53B.

INFLORESCENCE

Blooming habit: Continuous flowering throughout growing season; free and early blooming.

Size of umbel: 10–14 cm in diameter.

Borne: Umbel, flowers on pedicel, pedicel on peduncle, 7–10 cm above foliage.

Flowers:

*Form.*—Large, slightly cupped flowers have huge petals that overlap and in some instances curl upward to create a very ruffled appearance in the center of the flowers. The numerous petaloids help create this ruffled effect. Flowers are semi-double.

*Numbers of flowers per umbel.*—26–35.

*Size.*—Diameter: 5.0–6.0 cm. Depth: 1.7–2.0 cm; when tall petaloids are present depth is up to 3 cm.

Petals:

*Color.*—Each flower has two types of petals, upper and lower. The upper petals are cherry red with an electric orange at the base of the petals; the lower petals lack these orange highlights. Upper surface: Upper petals are 57A at outer edge shading to 50A and then to a more pronounced red-orange of 43A and 43B. Toward the base, the color shades to a softer orange of 43C and white 155B at the very base. Dark veining of 53B is prominent against the orange. Lower petals are 57A with highlights of 50A closer to base, fading to 50B and then to white 155B at the very base. Lower surface: Upper petals at 46C and 46D. The lower petals are 57B with highlights of 47B and 47C. Dark veining of 46B shows through. Shape: Oval to heart shaped. Size: 2.9–3.2 cm long; 2.4–3.6 cm wide. Apex: Rounded. Base: Pointed. Margin: Entire. Number per flower: 7–10. Texture and appearance: Velvety, smooth, highly reflective.

*Tonality from a distance.*—Large, showy flower heads of striking cherry-red with highlights of electric orange-red at the centers set above a mound of medium green foliage.

Petaloids:

*Quantity.*—0–8.

*Shape.*—Irregular; some twisted; tubular; petal shaped with cut margin; holding pollen.

*Color.*—Same as petals.

Pedicel:

*Length.*—3.0–4.0 cm.

*Color.*—184A with blush of 185A.

Peduncle:

*Length.*—13.5–16.0 cm.

*Color.*—146C shading to 144A at base where connects to stem with blush of 187C along peduncle.

Lasting quality: Umbels last 7–14 days.

Disease/pest resistance: No unusual susceptibility to diseases or pests has been noted to date.

REPRODUCTIVE ORGANS

Stamens:

*Anthers.*—2.5–3.0 mm.

*Filaments.*—Length: 8–10 mm. Color: Predominantly white; some with cherry-fuchsia pink blushing. Pollen: Golden orange.

Pistils:

*Number.*—One.

*Length.*—9–11 mm.

*Stigma.*—Number: One. Color: Deep, cherry-red.

*Style.*—Length: 3–4 mm. Color: Deep, cherry-red.

*Ovaries.*—Superior, mildly pubescent, 5–6 mm long, 2.0–2.5 mm wide; pale green.

Fruit: None observed.

I claim:

1. A new and distinct variety of geranium plant substantially as shown and described.

* * * * *

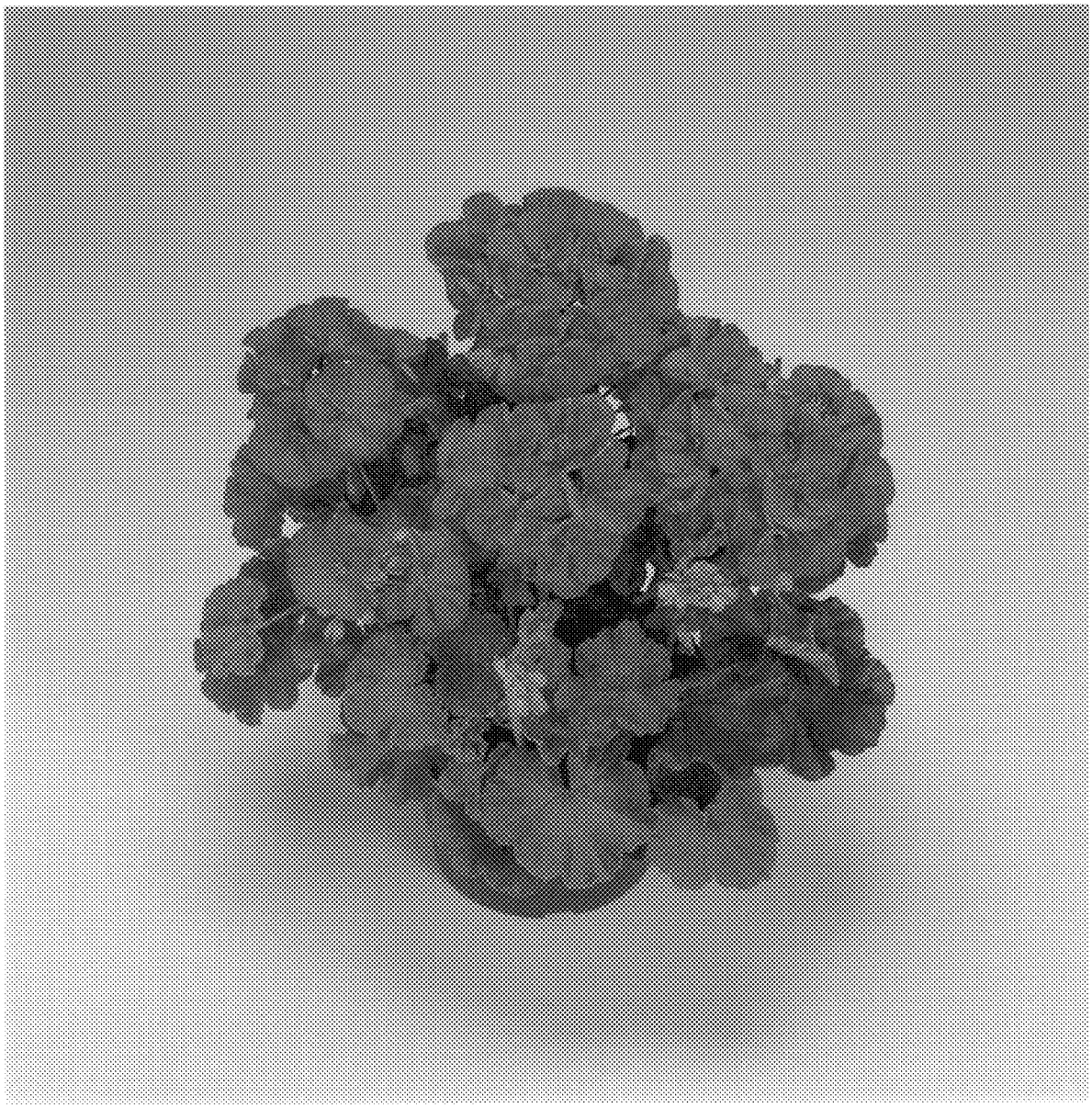

UNITED STATES PATENT AND TRADEMARK OFFICE

CERTIFICATE OF CORRECTION

PATENT NO. : PP 13,735 P2
DATED : April 22, 2003
INVENTOR(S) : David Lemon

It is certified that error appears in the above-identified patent and that said Letters Patent is hereby corrected as shown below:

Column 2,
Line 29, under "Stem", "Color.—114B." should read -- Color.—144B. --

Signed and Sealed this

Fourth Day of November, 2003

JAMES E. ROGAN
*Director of the United States Patent and Trademark Office*